United States Patent [19]

Colbaugh

[11] Patent Number: 4,605,959

[45] Date of Patent: Aug. 12, 1986

[54] PORTABLE COMMUNICATIONS TERMINAL

[75] Inventor: Michael E. Colbaugh, Trafford, Pa.

[73] Assignee: Westinghouse Electric Corp., Pittsburgh, Pa.

[21] Appl. No.: 643,503

[22] Filed: Aug. 23, 1984

[51] Int. Cl.⁴ .............................................. H04N 7/14
[52] U.S. Cl. .................... 358/93; 358/250; 455/606
[58] Field of Search ................ 358/93, 230, 241, 242, 358/250, 254, 255, 108; 455/347, 606

[56] References Cited

U.S. PATENT DOCUMENTS

| 3,542,457 | 11/1970 | Balding | 358/93 |
| 4,079,413 | 3/1978 | Yamashita | 358/241 |
| 4,106,283 | 8/1978 | Yamashita | 358/241 |
| 4,310,849 | 1/1982 | Glass | 358/250 |

OTHER PUBLICATIONS

*Aviation Week and Space Technology*, Oct. 11, 1982, pp. 133, 135, P. J. Klass, "Technique Benefits Novice Technicians".
University of Pittsburgh Thesis, 1980, M. E. Colbaugh, "A Computer Based, Real-Time Eye Movement Monitor".

*Primary Examiner*—Howard W. Britton
*Attorney, Agent, or Firm*—Daniel C. Abeles

[57] ABSTRACT

Portable communication terminal composed of a headset to be worn on the head of a user and a portable transceiver set to be carried by the user. The terminal includes a non-electrical optical fiber conductor mounted for transmitting optical images between the headset and the portable transceiver set; optical elements disposed at the headset for enabling an image transmitted to the headset from the transceiver set to be viewed by a user wearing the headset and for causing an image of the scene in front of a user wearing the headset to be formed at the transceiver set; a television transmitter and receiver at the transceiver set for transmitting a video signal and for forming a video display from signals conducted to the transmitter and receiver; and optical elements at the transceiver set disposed for supplying to the transmitter images formed at the transceiver set by light passing through the optical fiber conductor for conversion into a video signal, and for supplying to the transceiver set an image of the video display for transmission via the optical fiber conductor to the headset.

11 Claims, 1 Drawing Figure

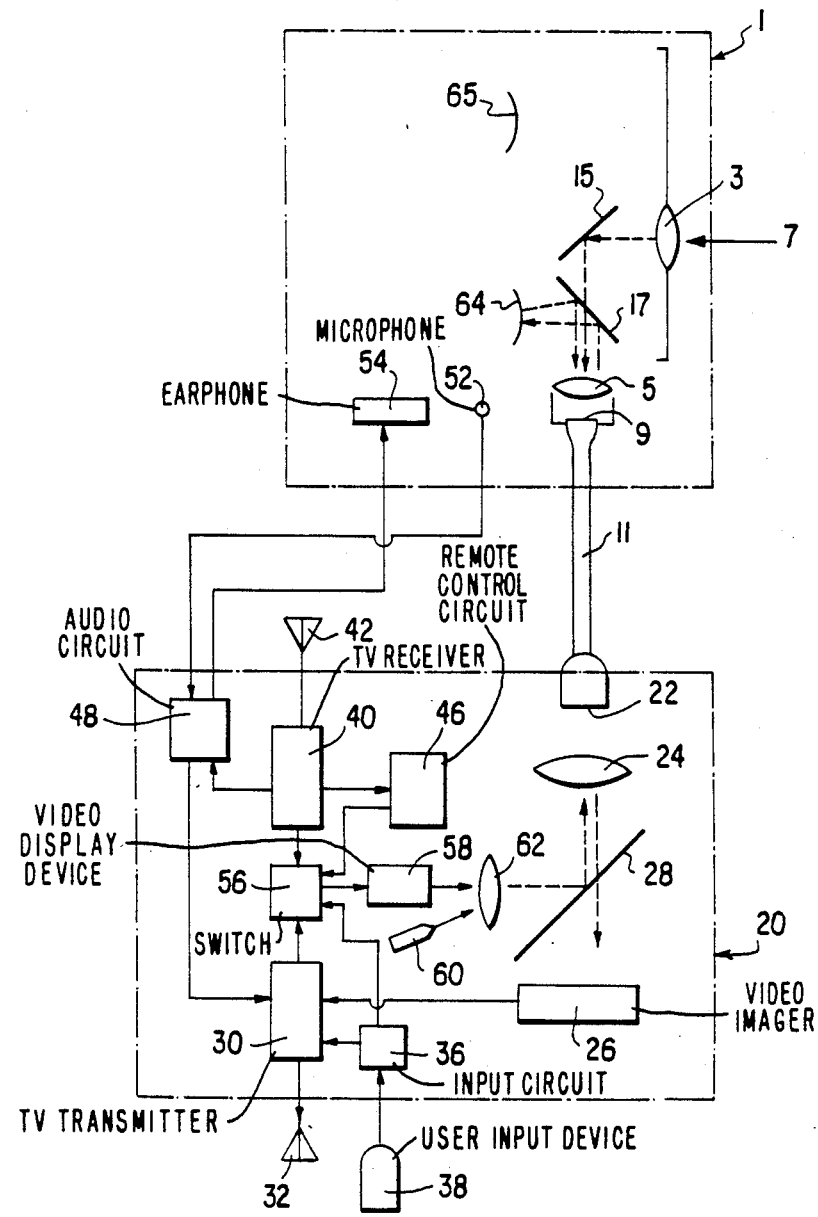

PORTABLE COMMUNICATIONS TERMINAL

BACKGROUND OF THE INVENTION

The present invention relates to portable communications terminals of the type capable of supplying a television display and two-way audio communication capability to a user.

A terminal which has previously been proposed by Honeywell, and which is designated "VIMAD", includes a helmet-like headset and an electronics package worn on the user's waist. The headset carries a small television display tube projecting onto an eyepiece to permit one eye of the user to view the television display. The electronics package contains a two-way radio, a miniature television receiver and batteries. The radio is connected to a microphone and earphone mounted in the headset, while the television receiver supplies video information to the display tube. This terminal was described in the periodical *Aviation Week & Space Technology*, Oct. 11, 1982.

There have also been proposals for eye motion recorders which permit recording of the motion of a subject's eyes relative to the scene being viewed. One such recorder, disclosed in U.S. Pat. No. 3,542,457, is in the form of a head-mounted unit including a first television camera aimed at the scene being viewed by the wearer, an optical system directing a spot of light onto the cornea of one eye of the user, and a second television camera associated with the optical system to record the light spot reflected from the cornea. The position of the reflected spot on the field of view of the second camera corresponds to the direction in which the user is looking. The images produced by the two cameras can be superimposed on one another.

SUMMARY OF THE INVENTION

It is an object of the present invention to provide an improved portable terminal which permits two-way audio and visual communication with a remote station while leaving the user's hands free to perform any necessary tasks.

Another object of the invention is to provide such a terminal with eye movement monitoring capability to permit a viewer of the video information transmitted by the terminal to observe the direction in which a user of the terminal is looking.

The above and other objects are achieved according to the invention by a portable communication terminal composed of a headset to be worn on the head of a user and a portable transceiver set to be carried by the user, the terminal including: a non-electrical optical fiber conductor mounted for transmitting optical images between the headset and the transceiver set; optical elements at the headset for enabling an image transmitted to the headset from the transceiver set to be viewed by a user wearing the headset and for causing an image of the scene in front of a user wearing the headset to be formed at the transceiver set; a television transmitter and receiver at the transceiver set for transmitting a video signal and for forming a video display from signals conducted to the transmitter and receiver; and optical elements at the transceiver set for supplying to the transmitter and reciever images formed at the transceiver set by light passing through the optical fiber conductor for conversion into a video signal, and for supplying an image of the video display formed by the transmitter and reciever for transmission via the optical fiber conductor to the headset.

In further accordance with the invention, an eye movement monitoring system is incorporated into the terminal. This system includes a monitoring light source disposed for directing a light beam at one eye of the user such that the light beam is reflected from the eye surface and is conducted from the headset via the optical fiber conductor to the transceiver set to form part of the video signal.

BRIEF DESCRIPTION OF THE DRAWING

The FIGURE is a partly pictorial and partly block circuit diagram of a preferred embodiment of a terminal according to the invention.

DESCRIPTION OF THE PREFERRED EMBODIMENTS

The upper portion of the FIGURE illustrates the components of the headset 1 of a unit according to the invention. These include an imaging lens 3 which cooperates with a further lens 5 to form an image of the scene 7 being viewed on an imaging plane 9 of a fiber optic bundle 11. The light traveling between lens 3 and lens 5 is reflected by a mirror 15 and part of the light passes through a semitransparent mirror or beam splitter 17. All light paths are shown as broken lines.

Images of scene 7 formed on plane 9 are conducted by bundle 11 to an imaging plane 22 in portable transceiver set 20. Such images are then focussed by a lens 24 onto a video image forming device 26, which is preferably a solid state video imager.

Part of the light traveling from lens 24 passes through a beam splitter 28 to imager 26.

Each of beam splitters 17 and 28 is located and oriented so that its plane, a surface, is at an angle of 45° to the, or each, light beam incident thereon so that substantially equal portions of the incident light energy will be transmitted and reflected. The reflected portion will then be reflected also at an angle of 45° to the beam splitter plane, or surface. These relations will exist regardless of which side of the beam-splitter faces the source of the light beam.

Imager 26 generates signals constituting a video image of scene 7 in front of the user and conducts those signals to a television transmitter 30 which can broadcast a television signal containing this information to a base station (not shown) via a transmitting antenna 32.

Transmitter 30 is additionally connected to receive signals form an auxiliary user input circuit 36 that can be actuated by a user input device 38 which will be described below.

Set 20 further includes a television receiver 40 connected to a receiving antenna 42 to receive television signals from the base station.

In the illustrated embodiment, over-the-air, or broadcast, television signal transmissions and reception are contemplated. However, the invention could also be implemented with other forms of signal transmission including, for example, an optical fiber link, a modulated light beam conducted through the air, or a microwave link.

Receiver 40 is constructed in the usual manner to provide, at separate output, video image signals and audio frequency signals based on information contained in the received television signals.

A remote control circuit 46 is connected to receiver 40 to respond to data or control signals transmitted to receiver 40 separately or with television signals from the base station for controlling the operation of various components in transceiver set 20. Circuit 46 can be constructed and connected to control any electrically controllable function of any of these components. Such remote control capability will serve to increase the possible uses of the terminal. One exemplary control function could be deactivating a particular operation within the terminal to preserve the security of information being transmitted. Another possible control function will be described in detail below.

An audio circuit 48 in set 20 is connected to conduct audio signals from a microphone 52 incorporated into set 1 to the audio input of transmitter 30. Audio circuit 48 further operates to conduct audio signals from receiver 40 to an earphone 54 in set 1.

An electrically controllable switch 56 is connected to receive the video image signals supplied to transmitter 30 from imager 26 and to receive video image signals provided by receiver 40 and to conduct a selected one of those video signals to a video display device 58. Input circuit 36 and remote control circuit 46 are each connected to control the operation of switch 56 to effect selection of the source of video signals for display device 58. Thus, such selection can be effected either by a suitable signal transmitted to circuit 46 from the remote station or by appropriate actuation of input device 38 by the users.

Other circuit functions can be controlled in a similar manner.

An infrared beam source 60 is associated with display device 58 so that an image produced by device 58 can be focussed, or reproduced, along with an infrared beam spot, on plane 22 via beam splitter 28 and lens 24. This optical system can be supplemented by a further lens 62 to adjust for the focal lengths required for retinal projection in set 1.

While the FIGURE shows, and the above description refers to, simple lenses 3, 5, 24 and 62, each of these elements can be constituted by a plural lens optical system constructed in a conventional manner to perform the desired focussing operation.

The infrared spot thus transmitted will impinge on the user's eye 64 and will be reflected back from the cornea in a direction dependent on the orientation of the eyeball, and thus the direction in which the user is looking can be determined. The direction of reflection will determine the point at which the reflected infrared beam impinges on plane 9 and thus the location of the infrared beam on the field of view of imager 26. Imager 26 is constructed, in a known manner, to be responsive to light radiation in the visible range and infrared radiation at the frequency of the beam produced by source 60.

Headset 1 preferably has a helmet-like form and is constructed to be worn by the user in such a manner that images formed on plane 9 by light conducted through fiber optic bundle 11 will be projected on the retina of the one eye 64 of the user, while the user's other eye 65 can directly view the scene 7 at the front of headset 1.

Eye movement monitoring capability is incorporated into the terminal and is accomplished according to known principles which have been the subject of research for a number of years. These principles are described, inter alia, in a graduate thesis entitled "A Computer Based, Real-Time Eye Movement Monitor" by the present inventor in 1980 while attending the University of Pittsburgh, Department of Electrical Engineering.

The eye monitoring system will allow an observer of the television picture transmitted via transmitter 30 to obtain an indication of the direction in which the user of the terminal is looking with respect to the scene 7 being viewed. The "observer" at the remote station could be a computer constructed to interpret a video display.

According to one significant feature of the present invention, all of the electronics are mounted in transceiver set 20, i.e. headset 1 includes essentially only optical elements and audio components which need not be provided with a source of electrical power at the headset itself.

This form of construction offers a number of significant advantages, including the fact that the weight of headset 1 can be minimized, set 1 contains no sources of heat which could cause user discomfort, and the danger of electrical shock is minimized.

In the operation of the illustrated system, an image of the scene 7 being viewed is combined, at imaging plane 9, with the infrared beam reflected from the user's cornea, and light travels from plane 9 via bundle 11 to imaging plane 22, the image then being formed on plane 22 being focussed by lens 24 on the receiving surface of imager 26. Imager 26 forms, in a known manner, a video signal which is conducted to transmitter 30 and is then broadcast via antenna 32 to a remote base station.

The system can be operated to also transmit the video signal generated by imager 26 via transmitter 30 directly to video display 58. The resulting image of scene 7 is then conducted via beam splitter 28, lens 24, imaging plane 22, fiber optic bundle 11, imaging plane 9, lens 5 and beam splitter 17 to be projected on the retina of eye 64. In this case, both eyes 64 and 65 will view scene 7. In accordance with the invention, lens 3 can be positioned so that when an image of scene 7 is being projected on the retina of eye 64, the scene will be viewed by the user stereoscopically. In fact, lens 3 can be laterally spaced from the location of eye 65 so that when the image projected on the retina of eye 64 is that of the scene in the field of view of lens 3, the stereoscopic effect can be enhanced.

Alternatively, when the image being viewed by eye 64 is based on a video signal supplied to receiver 40 from a remote base station, this image can be in the form of a computer generated display containing relevant information relating to the scene being viewed.

The system according to the invention could be used to assist a wide variety of activities including repair of complex electronic or mechanical equipment, disarming of explosives or surgical procedures, where the user of the terminal would undertake the necessary procedure under guidance of an expert located at the remote station, viewing a video display of scene 7 and communicating with the user via the audio system. The individual at the remote station would be additionally aided by a spot on the video display indicating the direction in which the user is looking.

Lens 62 in transceiver set 20 can be adjusted to assure correct focussing of the image being transmitted to eye 64.

Existing technology can be used to supply the user with a color image having good resolution. To assure proper resolution, fiber optic bundle 11 should have a number of picture elements, or individual fibers, equal to at least four times the acceptable number of picture elements associated with the video display 58 in order to preserve picture quality.

At the remote base station (not shown) there can be provided all video and text information that the user may require to perform the particular task in question. Appropriate information can be requested via the voice link. Text information could be made available to the user via the video link.

Input device 38 may be, for example, one or more push-buttons mounted on set 20 or a foot switch and can be operated by the user to signal a particular scene element at which he is then looking. The resulting signal is then transmitted, together with the television signal, to draw the attention of a viewer at the remote station to the particular scene element.

Preferably, all of the components of set 1 which are directly in front of eye 64 are mounted as an assembly which can be moved out of the user's field of view when desired.

It will be understood that the above description of the present invention is susceptible to various modifications, changes and adaptations, and the same are intended to be comprehended within the meaning and range of equivalents of the appended claims.

I claim:

1. Portable communication terminal composed of a headset to be worn on the head of a user and a portable transceiver set to be carried by the user, said terminal comprising: non-electrical optical fiber means mounted for transmitting optical images between a location at said headset and a location at said portable transceiver set; first optical means disposed at said headset for enabling an image transmitted to said location at said headset from said location at said transceiver set to be viewed by a user wearing said headset; second optical means disposed at said headset and associated with said location at said headset for causing an image of the scene in front of a user wearing said headset to be formed at said location at said transceiver set; television transmitter and receiver means at said transceiver set for transmitting a video signal and for forming a video display from signals conducted to said transmitter and receiver means; and third optical means at said transceiver set disposed between said transmitter and receiver means and said location at said transceiver set for supplying to said transmitter and receiver means images formed at said location at said transceiver set by light passing through said optical fiber means for conversion into a video signal, and for supplying to said location at said transceiver set an image of the video display formed by said transmitter and receiver means for transmission via said optical fiber means to said location at said headset.

2. An arrangement as defined in claim 1 further comprising eye movement monitoring means composed of a monitoring light source disposed for directing a light beam at one eye of the user such that the light beam is reflected from the eye surface onto said location at said headset for transmission via said optical fiber means to said location at said transceiver set and then to said television transmitter and receiver means.

3. An arrangement as defined in claim 2 wherein said monitoring light source is disposed at said transceiver set for so directing a light beam at one eye of the user via said third optical means and said optical fiber means.

4. An arrangement as defined in claim 1 further comprising an audio system composed of a microphone and a speaker at said headset and audio signal transmitting and receiving means located at said transceiver set and electrically connected to said microphone and said speaker.

5. An arrangement as defined in claim 4 wherein said audio signal transmitting and receiving means are electrically connected to said television transmitter and receiver means.

6. An arrangement as defined in claim 1 wherein said television transmitter and receiver means are operative for selectively forming the video display from the video signal produced from images formed at said location at said transceiver set by light passing through said optical fiber means so that the image viewed by the user is that of the scene in front of the user.

7. An arrangement as defined in claim 1 wherein said television transmitter and receiver means are operative for selectively forming the video display from a video signal transmitted to said transmitter and receiver means from a remote station.

8. An arrangement as defined in claim 1 further comprising signalling means disposed to be operated by the user and connected to said television transmitter and receiver means for adding to the video signal transmitted by said transmitter and receiver means an identification signal resulting from operation of said signalling means by the user.

9. An arrangement as defined in claim 1 further comprising signalling means disposed to be operated by the user and connected to said television transmitter and receiver means for controlling the operation of said television transmitter and receiver means.

10. An arrangement as defined in claim 1 further comprising remote control means connected to said television transmitter and receiver means for receiving control signals from said television transmitter and receiver means and for controlling the operation of said television transmitter and receiver means.

11. An arrangement as defined in claim 1 wherein said television transmitter and receiver means comprise a television transmitter for transmitting the video signal to a remote station, and a television receiver for receiving, from a remote station, signals for forming the video display.

* * * * *